United States Patent
Bintig et al.

(10) Patent No.: US 9,827,585 B2
(45) Date of Patent: Nov. 28, 2017

(54) STICK APPLICATOR

(75) Inventors: Janine Bintig, Zurich (CH); Edmund Bonna, Triesenberg (CH)

(73) Assignee: SIKA TECHNOLOGY AG, Baar (CH)

( * ) Notice: Subject to any disclaimer, the term of this patent is extended or adjusted under 35 U.S.C. 154(b) by 87 days.

(21) Appl. No.: 14/241,588

(22) PCT Filed: Aug. 30, 2012

(86) PCT No.: PCT/EP2012/066852
§ 371 (c)(1),
(2), (4) Date: Feb. 27, 2014

(87) PCT Pub. No.: WO2013/030270
PCT Pub. Date: Mar. 7, 2013

(65) Prior Publication Data
US 2014/0193188 A1 Jul. 10, 2014

(30) Foreign Application Priority Data

Aug. 31, 2011 (EP) ..................................... 11179551

(51) Int. Cl.
*A61M 35/00* (2006.01)
*B05C 1/00* (2006.01)
(Continued)

(52) U.S. Cl.
CPC ............... *B05C 1/00* (2013.01); *B43M 11/06* (2013.01); *B65D 47/42* (2013.01); *A61M 35/003* (2013.01); *A61M 35/006* (2013.01)

(58) Field of Classification Search
CPC .................................................. A61M 35/006
(Continued)

(56) References Cited

U.S. PATENT DOCUMENTS 3,152,352 A 10/1964 Kosik, Jr.
3,720,341 A 3/1973 Greenfield et al.
(Continued)

FOREIGN PATENT DOCUMENTS

EP 2220934 A1 8/2010
JP 60-170901 U 11/1985
(Continued)

OTHER PUBLICATIONS

International Search Report (English and German) and Written Opinion of the ISA (German) for PCT/EP2012/066852, ISA/EP, Rijswijk, NL, dated Jan. 17, 2013.
(Continued)

*Primary Examiner* — David Walczak
*Assistant Examiner* — Joshua Wiljanen
(74) *Attorney, Agent, or Firm* — Buchanan Ingersoll & Rooney PC

(57) ABSTRACT

A stick applicator for applying a liquid stored in a hard ampoule, comprising a hollow plastic stick body, designed for receiving the ampoule and having a closed end and an open end, the wall of which is sufficiently flexible to allow the ampoule held in the plastic stick body to be broken without using an implement and thereby let the liquid out into the interior of the plastic stick body, and comprising an applicator head, which is fitted on the open end of the plastic stick body and comprises a foam, felt or fibre body, wherein the plastic stick body has at least in certain portions a separate sheathing layer to increase its perforation resistance to ampoule fragments and near its open end retaining means for securely holding the applicator head and/or retaining means for securely holding the ampoule inside it.

17 Claims, 2 Drawing Sheets

(51) Int. Cl.
*B43M 11/06* (2006.01)
*B65D 47/42* (2006.01)
*A61F 13/40* (2006.01)

(58) Field of Classification Search
USPC .......................................... 401/132, 133, 196
See application file for complete search history.

(56) References Cited

U.S. PATENT DOCUMENTS

| | | | |
|---|---|---|---|
| 3,764,796 | A | 10/1973 | Gilliam et al. |
| 3,876,314 | A * | 4/1975 | Nehring ............... A61M 35/006 401/133 |
| 4,572,689 | A | 2/1986 | Chernack |
| 4,957,385 | A | 9/1990 | Weinstein |
| 5,098,297 | A * | 3/1992 | Chari et al. ................ 433/215 |
| 5,445,462 | A * | 8/1995 | Johnson ............... A61M 35/006 401/132 |
| 5,908,256 | A * | 6/1999 | Bernstein ............... A45D 34/04 401/136 |
| 6,039,488 | A * | 3/2000 | Krawczyk et al. ........... 401/132 |
| 6,340,097 | B1 * | 1/2002 | D'Alessio et al. .......... 401/132 |
| 6,478,191 | B1 | 11/2002 | D'Alessio et al. |
| 6,991,394 | B2 | 1/2006 | Tufts et al. |
| 7,182,536 | B2 | 2/2007 | Tufts et al. |
| 7,744,299 | B1 * | 6/2010 | Greer, Jr. ............... B05C 17/002 401/266 |
| 2001/0042553 | A1 | 11/2001 | Duqueroie |
| 2002/0076255 | A1 | 6/2002 | Hoang et al. |
| 2003/0015557 | A1 | 1/2003 | D'Alessio et al. |
| 2004/0179888 | A1 | 9/2004 | Tufts et al. |
| 2005/0175786 | A1 | 8/2005 | Singh et al. |
| 2006/0072959 | A1 | 4/2006 | Tufts et al. |
| 2013/0108352 | A1 * | 5/2013 | Ruiz et al. .................. 401/132 |
| 2014/0003858 | A1 * | 1/2014 | Frazier ........................ 401/133 |

FOREIGN PATENT DOCUMENTS

| | | |
|---|---|---|
| JP | 10-070974 A | 3/1998 |
| JP | 2002-028557 A | 1/2002 |
| JP | 3118986 U | 1/2006 |
| JP | 2006512975 A | 4/2006 |
| JP | 2006-206135 A | 8/2006 |
| JP | 2007161342 A | 6/2007 |
| JP | 2009120509 A | 6/2009 |
| JP | 2009189610 A | 8/2009 |
| JP | 2010-260581 A | 11/2010 |
| JP | 2011-163473 A | 8/2011 |
| WO | 00/38564 A1 | 7/2000 |
| WO | 2004062709 A2 | 7/2004 |

OTHER PUBLICATIONS

Office Action (Notice of Reasons for Rejection) dated Jul. 26, 2016, by the Japanese Patent Office in corresponding Japanese Patent Application No. 2014-527655, and an English Translation of the Office Action. (8 pages).

Office Action (Notification of the Second Office Action) dated Aug. 15, 2016, by the Chinese Patent Office in corresponding Chinese Patent Application No. 201280042173.9, and an English Translation of the Office Action. (20 pages).

Office Action (Notification of the Third Office Action) dated May 11, 2017, by the State Intellectual Property Office of the People's Republic of China in corresponding Chinese Patent Application No. 201280042173.9 (19 pages including a partial English Translation).

Office Action (Notice of Reasons for Rejection) dated Jul. 18, 2017, by the Japanese Patent Office in Japanese Patent Application No. 2014-527655, and an English Translation of the Office Action. (10 pages).

* cited by examiner

STICK APPLICATOR

CROSS-REFERENCE TO RELATED APPLICATIONS

This application is a 371 U.S. National Stage of International Application No. PCT/EP2012/066852, filed Aug. 30, 2012, which claims priority to European Patent Application 11179551.4, filed Aug. 31, 2011. The disclosures of the above applications are incorporated herein by reference.

TECHNICAL FIELD

The present invention relates to a stick applicator for discharging a liquid stored in a hard ampule of, for example, a primer or activator agent for pretreating surfaces to be provided with an adhesive. Such a stick applicator has a hollow plastic stick body designed to receive the ampule, and includes a closed end and an open end, the wall of which is sufficiently flexible to allow the ampule held in the plastic stick body to be broken and thereby cause the liquid to escape into the interior of the plastic stick body, and an applicator head which is fitted on the open end of the plastic stick body and which comprises a foam, felt or fiber body.

PRIOR ART

Pretreatment agents for producing adhesive joints are normally offered in packaging that consists of an aluminum bottle, a polyethylene (PE) bowl and a screw cap for the bottle made of polypropylene (PP). For single-use applications, aluminum tubes or primer sticks and activator pads are offered, each having very limited contents.

Stick applicators of the aforementioned type have also been commercially available and in practical use for a long time. Certain products of this type are provided with a special tool for rupturing the ampule held in the stick applicator in order to release the fluid contained therein; cf. for example, WO 2000/038564. This tool is used to apply a heavy pressure locally on the plastic wall of the stick body. The wall need exhibit only one degree of deformability which enables the force applied with the tool to be introduced into the fragile wall of the ampule (generally of glass), thus it can be relatively stiff. This prevents shards formed during rupture of the ampule from being able to penetrate the stick body and cause injury to the user.

From the perspective of the inventor, however, a stick body that is too stiff is, in terms of its handling, problematic in several respects. In particular, the use of such a stick applicator requires virtually of necessity the use of the aforementioned tool in order to rupture the ampule, while simpler manipulations (such as rupturing the ampule by bending the stick over the edge of a table or by hand) are ruled out.

Thus, the object of the present invention is to provide an improved stick applicator of the generic kind which is in particular easy, flexible and safe to use.

DISCLOSURE OF THE INVENTION

This object is achieved by a stick applicator having the features of claim 1. According to a second, relatively independent aspect of the invention, a stick applicator having the features of claim 7 is provided. Useful further developments of the inventive concept are the subject matter of the dependent claims.

The wall of the stick applicator, reinforced according to the first aspect of the present invention by the additional sheathing, yet remaining flexible nevertheless, offers a high degree of safety when handled and at the same time the possibility, by exerting a specific pressure, of increasing the flow of the product through the applicator head and to control it to a certain degree.

In one implementation of the present invention according to the first aspect, a separate sheathing layer is provided which functions simultaneously as an inscription holder. As stick applicators of the aforementioned kind are normally provided with a label for purposes of marking, realization of the present invention allows for this with practically no additional production effort.

In another implementation of the separate sheathing layer extends over the entire handle region of the plastic stick body. This makes possible a particularly flexible handling of the stick in accordance with the respective finger dexterity and habits of the user while ruling out the risk of injury.

A further implementation provides that the separate sheathing layer is adhesively bonded to the outer wall of the plastic stick body. In this case, the application of the sheathing layer is largely similar to that of a conventional adhesive label and in particular can be implemented using available equipment. In principle, however, a shrink tubing or a conventional roll-up tube with merely local adhesion or welding on the primary sheathing of the stick may also be used.

In a further implementation the separate sheathing layer is formed from a polypropylene or similar film. In addition to polypropylene, other materials such as polyethylene also come under consideration.

In other implementations the separate sheathing layer is single or multi-layered (for example, double-layered) in design and has a total thickness in the range of between 80 and 160 μm, in particular in the range of between 100 and 140 μm. However, other wall thicknesses of the separate sheathing layer may also be expedient, depending on the choice of specific material as well as the material and thickness of the wall of the stick body itself.

In the implementation according to the relatively independent second aspect of the invention, the plastic stick body is cylindrically shaped in the region of its open end, and the applicator head includes an annular groove in which the open end of the plastic stick body engages. In this configuration, retaining means having a barbed-hook effect for securely holding the applicator head on the plastic stick body and/or the ampule in the plastic stick body against an axial, forwardly acting force are formed on the exterior surface and/or interior surface of the plastic stick body at or near the open end thereof.

Projections in the interior of the stick body prevent the user in particular from removing an ampule from the stick again once it is inserted (and possibly injuring him/herself), but at the same time also an unintentional ejection of the ampule from the front end of the stick, in case the user suddenly moves the stick axially in a forward direction in order to advance the liquid flow. Similarly, snap-in hooks or a thread section formed on the outside of the stick body prevent the applicator head in the event of sudden movements of the stick from detaching from the stick body and thereby becoming lost and allowing the fluid contained in the stick body to escape uncontrollably.

For one, the thread section may be formed at the open end of the stick body while essentially retaining the normal wall thickness (and flexibility) of the latter. In another implementation, recesses may be provided in the screw threads which increase substantially the elasticity of the front end of the stick body. In this way an additional suction effect relative to the product present in the interior of the stick body, and with that a boost to or certain controllability of the product flow may be achieved.

A further implementation of the present invention provides that the thread section formed on the exterior surface is closed over its entire circumference by local thinning in such a way that no fluid can escape through it, while largely retaining the advantages resulting from the enhanced elasticity of the open end of the stick.

In a further implementation, the thread section is designed with sharp edges for securely holding the applicator head in place. This makes it easier to cut into the material of the applicator head when the latter is screwed onto the stick, and increases the retention force. In addition, it can be provided that the angle of inclination of the thread flanks is smaller toward the open end of the stick body than toward the closed end, thus imparting to the thread section a kind of barb-hooked characteristic.

Corresponding to the aforementioned thread section on the stick body is an annular groove milled into the applicator head or an annular cut (easy and more cost efficient to produce) in which the thread section engages when the applicator head is screwed onto the stick body.

In both aspects of the present invention the retaining means or projections for holding or securing the ampule in place may be formed by impressions made from the outside in the wall of the stick body, which transform a small, for example, essentially strip-like section of the wall material (without the use of additional materials) into the aforementioned retaining means or projection.

BRIEF DESCRIPTION OF THE DRAWINGS

Advantages and functionalities of the present invention will become apparent from the following description of preferred exemplary embodiments with reference to the figures, in which:

FIG. 1 shows a stick applicator 10 for areal application of a primer packaged in an ampule 11 for pretreating adhesive surfaces, which comprises a plastic stick body 13 and a foam applicator head 15. The ampule 11 consists of glass and the plastic stick body 13, for example, of polyamide (PA), PE or PP. An annular rib 13a on the stick body 13 is provided as a stop for the applicator head 15 to be slid on from the open end of the stick body. Like the stick body 13, the applicator head 15 consisting completely of foam also has a cylindrical base form. Incorporated in the latter is an annular groove 15a, the diameter of which is the same as that of the stick body 13, such that the open end of the stick body engages in said groove when the applicator head is attached. Moreover, it is noted that the term "stick applicator" is also understood to mean applicators that are not basically cylindrical in shape, but rather have, for example, a rounded, prismatic, bulbous or some other shape that is nevertheless suitable for the intended use.

The central region of the stick body 13 is wrapped with a PP adhesive film 13b for the purpose of strengthening its perforation resistance. The PP adhesive film 13b as a separate sheathing layer not only has a strengthening effect, but it also functions as an inscription holder for product labelling, manufacturer specifications, user instructions, etc. In the implementation shown it is single layered and has a thickness of 120 µm, but may also be double-layered, formed from a 60 µm film.

Figure 1:
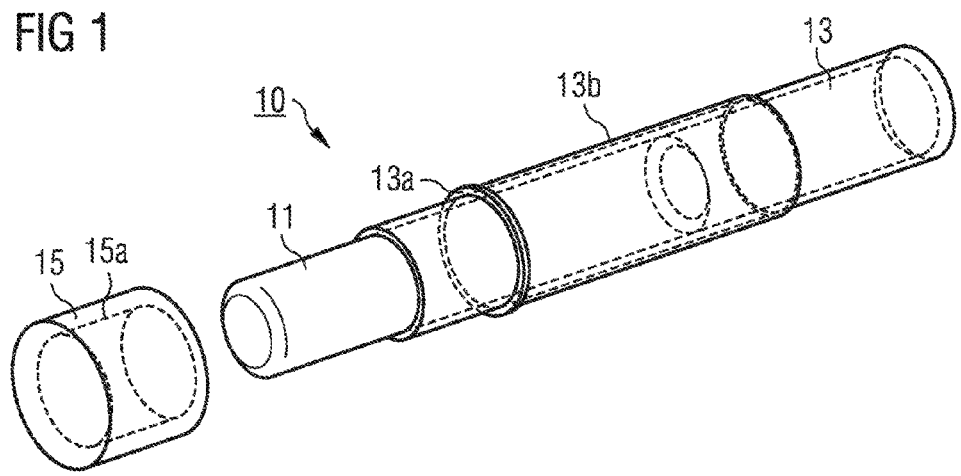
FIG. 1 shows in an outline perspective view (exploded view) a stick applicator according to the present invention.
Figure 2:
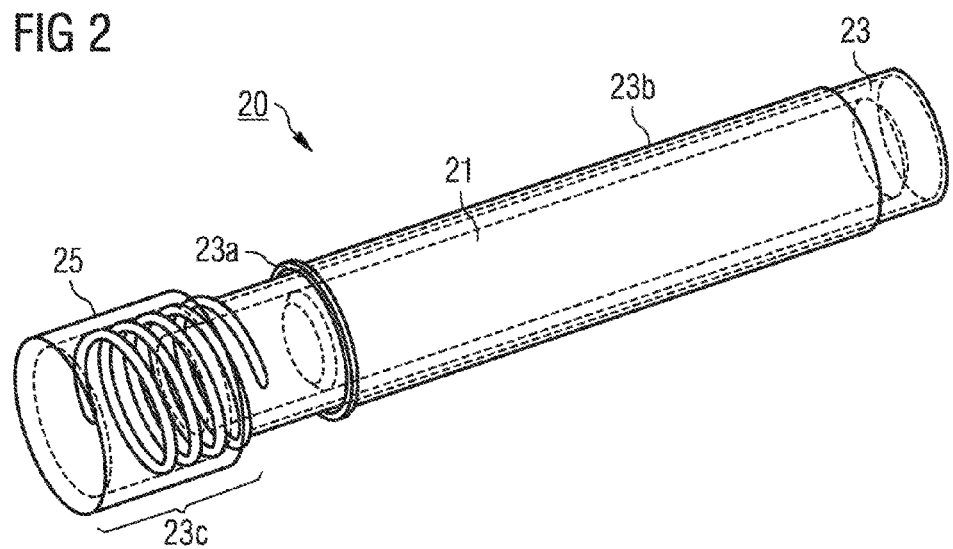
FIG. 2 shows a further perspective view, patterned after an "X-ray image", of a stick applicator according to the present invention.

FIG. 2 shows a modified embodiment of a stick applicator 20 in the assembled state, namely, patterned after an X-ray image. Parts that are identical or functionally equivalent to the implementation according to FIG. 1 are designated by reference numerals taken from FIG. 1 and are not further discussed. The configuration according to FIG. 2 differs initially from that of FIG. 1 in that the separate sheathing layer 23b made of a reinforcing PP film encases nearly the entire length of the stick body 23 made of a "soft" plastic. In addition, a thread section 23c is provided at the open end of the stick body 23 which serves to better secure the applicator head 25 to the stick body. The annular rib 23a is positioned in such a way that it prevents the applicator head from slipping too far to the rear when severely pressed by the user and under corresponding severe deformation of the elastic thread section 23c.

Figure 3:
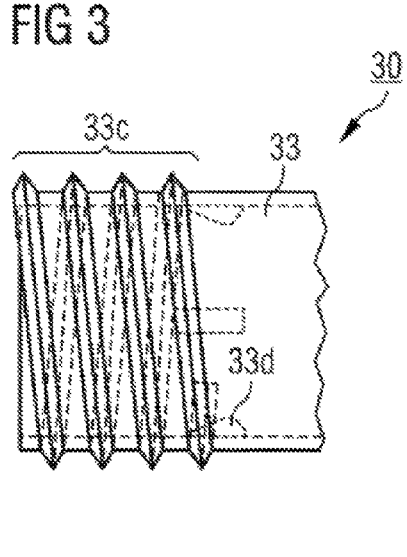
FIG. 3 shows a detailed view of the open end of the plastic stick body of a stick applicator according to the present invention.

FIG. 3 shows in a detailed view, again patterned after an X-ray image, the open end of the plastic stick body 33 of a further stick applicator 30. The stick body again includes a thread section 33c on the outer surface thereof designed with sharp edges and thread flanks that are geometrically symmetrical. Formed on the interior wall of the stick body are inwardly directed projections 33d, which are "asymmetrically" designed insofar as the flanks thereof directed toward the open end of the stick body have a smaller angle of inclination in relation to the inner surface of the sheathing than do the flanks facing the closed end of the stick body. In addition, the apex of the projections 33d is rounded. Thus, the projections 33d, when an ampule (not shown) is introduced in the stick body, may be relatively easily surmounted by the ampule, whereas they hold the ampule securely in place when impacted by axial, forwardly acting forces. In addition, the specific shape of the projections allows for easy removal from the injection molding tool used to produce the plastic stick body. Moreover, in some cases such removal may be further facilitated by the flexibility of the stick body.

Figure 4:
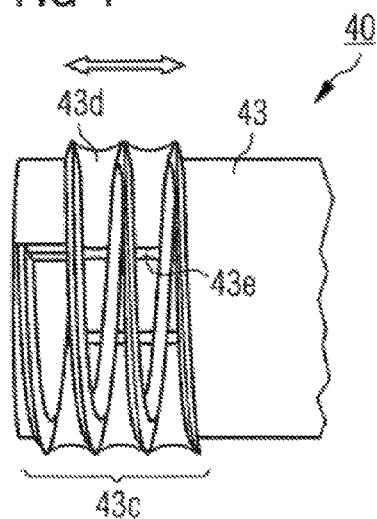
FIG. 4 shows a detailed view of the open end of the plastic stick body of another stick applicator according to the present invention.

FIG. 4 shows as a further modified implementation the front end of the stick body 43 of a further stick applicator 40. In this case, a thread section 43c is provided which may be elastically deformed by thinned annular sections 43d, between which individual stronger ribs 43e remain. The added elasticity of the front end of the stick created by this thread configuration allows for improved handling of the stick applicator, specifically a stronger compression of the foam material of the applicator head and, as a result, an enhanced suction effect of the foam for the fluid that has accumulated in the interior of the stick once the ampule has been ruptured, which is discharged via the applicator head and distributed on a surface. On the other hand, the circumferential surface of the thread section, which is also closed completely in the area of the thinned sections, prevents an unwanted lateral discharge of liquid retained in the stick body.

Figure 5:
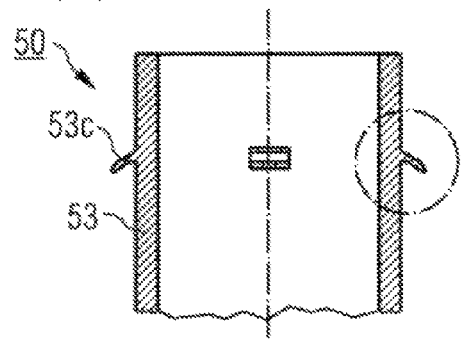
FIGS. 5 and 5A show cross-sectional views (FIG. 5A as a cut-out) of the open end of a further embodiment of the stick applicator according to the present invention.
Figure 5A:
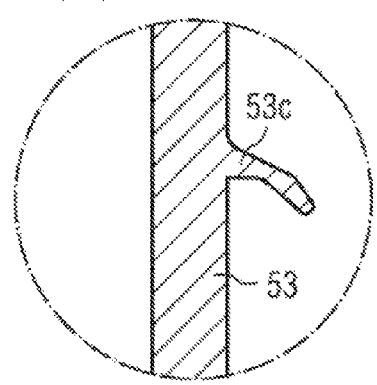

FIGS. 5 and 5A show the open end of the stick body 53 of a further stick applicator 50, in which individual, rearwardly inclined snap-in hooks 53c on the outer surface assume the function of the thread section in the above described implementations, that is, the function of securely holding the attached applicator head (not shown). FIG. 5A shows more precisely the geometry of said snap-in hooks in a specific configuration. The specific geometry facilitates a targeted yielding under an axial pressure operating from the open end (as occurs when the applicator head is attached), but offers on the other hand a relatively high resistance to a force acting in the direction toward the open end. Thus, the snap-in hooks increase the security of the applicator head against loss, even under "rough" handling by the user.

The implementation of the invention is not limited to these examples, but rather is also possible in a variety of modifications which fall within the practice of persons skilled in the art.

What is claimed Is:

1. A stick applicator for discharging a liquid stored in a hard ampule, having a hollow plastic stick body designed for receiving the ampule and including a closed and an open end, the wall of the hollow plastic stick body being sufficiently flexible to allow the ampule held in the plastic stick body to be ruptured, thereby causing the liquid to escape into the interior of the plastic stick body, and an applicator head which is attached to the open end of the plastic stick body and which comprises a foam, felt or fiber body,
    wherein the plastic stick body is cylindrically shaped at least in the region of its open end and the applicator head includes an annular groove or an annular cut into which the open end of the plastic stick body engages,
    wherein a thread section is formed on the outer surface of the plastic stick body at or near the open end thereof, for securely holding the applicator head on the plastic stick body, and
    wherein the plastic stick body includes projections formed on an inner surface of the plastic stick body at or near the open end thereof, said projections configured to securely hold the ampule in the plastic stick body against an axial, forward acting force.

2. The stick applicator according to claim 1, wherein the projections have a rounded saw-toothed shape including first and second inclined sections, the first section inclined toward the open end of the plastic stick body and having an angle of inclination smaller than an angle of inclination of the second section inclined toward the closed end.

3. The stick applicator according to claim 1, wherein the projections are formed on the interior wall.

4. The stick applicator according to claim 1, wherein the plastic stick body includes at least in sections a separate sheathing layer for strengthening its perforation resistance to ampule fragments and near its open end retaining means for securely holding the applicator head and/or retaining means for securely holding the ampule in the interior thereof.

5. The stick applicator according to claim 4, wherein the separate sheathing layer functions simultaneously as an inscription carrier.

6. The stick applicator according to claim 4, wherein the separate sheathing layer is adhesively bonded to the outer wall of the plastic stick body.

7. The stick applicator according to claim 4, wherein the separate sheathing layer is formed from a polypropylene or similar film.

8. The stick applicator according to one claim 4, wherein the separate sheathing layer is single or multi-layered and has a total thickness in the range of between 80μm and 160μm.

9. The stick applicator according to claim 4, wherein the retaining means for securely holding the ampule is designed as the projections on the inner surface.

10. The stick applicator according to claim 1, wherein the thread section formed on the outer surface is designed to be elastically deformable as a result of locally thinned sections or recesses in the wall.

11. The stick applicator according to claim 10, wherein the thread sections with locally thinned sections formed on the outer surface is closed over its entire circumference such that no liquid is able to escape through it.

12. The stick applicator according to claim 1, wherein the thread section is designed with sharp edges for securely holding the applicator head.

13. A stick applicator for discharging a liquid stored in a hard ampule, having a hollow plastic stick body designed for receiving the ampule and including a closed and an open end, the wall of the hollow plastic stick body being sufficiently flexible to allow the ampule held in the plastic stick body to be ruptured, thereby causing the liquid to escape into the interior of the plastic stick body, and an applicator head which is attached to the open end of the plastic stick body and which comprises a foam, felt or fiber body,
    wherein the plastic stick body is cylindrically shaped at least in the region of its open end and the applicator head includes an annular groove or an annular cut into which the open end of the plastic stick body engages,
    wherein formed on the inner surface of the plastic stick body at or near the open end thereof are projections for securely holding the ampule in the plastic stick body against an axial, forward acting force, and
    wherein the projections have a rounded saw-toothed shape including first and second inclined sections, the first section inclined toward the open end of the plastic stick body and having an angle of inclination smaller than an angle of inclination of the second section.

14. The stick applicator according to claim 13, wherein a thread section is formed on the outer surface of the plastic stick body at or near the open end thereof, for securely holding the applicator head on the plastic stick body.

15. The stick applicator according to claim 14, wherein the thread section formed on the outer surface is designed to be elastically deformable as a result of locally thinned sections or recesses in the wall.

16. The stick applicator according to claim 15, wherein the thread section with locally thinned sections formed on the outer surface is closed over its entire circumference such that no liquid is able to escape through it.

17. The stick applicator according to claim 14, wherein the thread section is designed with sharp edges for securely holding the applicator head.

* * * * *